(12) United States Patent
Van Halsema et al.

(10) Patent No.: US 9,681,636 B2
(45) Date of Patent: Jun. 20, 2017

(54) DETECTOR SYSTEM, SENSOR AND DAIRY ANIMAL TREATMENT DEVICE

(71) Applicant: LELY PATENT N.V., Maassluis (NL)

(72) Inventors: Frans Emo Diderik Van Halsema, Veenendaal (NL); Pieter Gerlof De Groot, Giessenburg (NL); Hélèna Geralda Maria Vijverberg, Maassluis (NL)

(73) Assignee: LELY PATENT N.V., Maassluis (NL)

(*) Notice: Subject to any disclaimer, the term of this patent is extended or adjusted under 35 U.S.C. 154(b) by 0 days.

(21) Appl. No.: 15/377,686

(22) Filed: Dec. 13, 2016

(65) Prior Publication Data
US 2017/0086421 A1    Mar. 30, 2017

Related U.S. Application Data

(60) Division of application No. 14/158,900, filed on Jan. 20, 2014, now Pat. No. 9,535,008, which is a
(Continued)

(30) Foreign Application Priority Data

Jul. 20, 2011    (NL) ..................................... 2007149

(51) Int. Cl.
*G01N 25/20* (2006.01)
*G01J 5/00* (2006.01)
(Continued)

(52) U.S. Cl.
CPC . *A01J 7/04* (2013.01); *A01J 5/01* (2013.01); *B25J 9/1679* (2013.01); *B25J 9/1697* (2013.01);
(Continued)

(58) Field of Classification Search
USPC ......................... 374/141, 148, 147, 121, 43
See application file for complete search history.

(56) References Cited

U.S. PATENT DOCUMENTS 3,874,337 A * 4/1975 Umbaugh ............. A01J 5/0133
119/14.15
6,073,580 A    6/2000 Graupner et al.
(Continued)

FOREIGN PATENT DOCUMENTS

DE    2759126    7/1979
DE    19630146    1/1998
(Continued)

OTHER PUBLICATIONS

International Preliminary Report on Patentability of PCT/NL/2012/050475 issued on Jan. 21, 2014.
(Continued)

*Primary Examiner* — Mirellys Jagan
(74) *Attorney, Agent, or Firm* — Oblon, McClelland, Maier & Neustadt, L.L.P.

(57) ABSTRACT

Sensor system with a sensor device having a through-flow cell for liquid, a detector device for measuring a property of the liquid in the through-flow cell and for generating an associated detector signal, a sensor control for analyzing the detector signal, wherein the sensor control detects a liquid transition between two different liquids in the through-flow cell when a change (per unit time) in the detector signal is greater than a threshold value. In the case of such a liquid transition detection, the sensor control generates an alarm signal. Liquid transition detection is carried out by optical, temperature and/or conductivity sensors.

19 Claims, 3 Drawing Sheets

Related U.S. Application Data continuation of application No. PCT/NL2012/050475, filed on Jul. 5, 2012.

(51) Int. Cl.
| | | |
|---|---|---|
| *A01J 7/04* | (2006.01) | |
| *G01N 21/59* | (2006.01) | |
| *G01N 21/05* | (2006.01) | |
| *G01K 1/02* | (2006.01) | |
| *G01N 21/85* | (2006.01) | |
| *B25J 9/16* | (2006.01) | |
| *B25J 11/00* | (2006.01) | |
| *A01J 5/01* | (2006.01) | |
| *G06K 9/00* | (2006.01) | |
| *G08B 21/18* | (2006.01) | |
| *G05D 7/06* | (2006.01) | |

(52) U.S. Cl.
CPC ............ *B25J 11/0045* (2013.01); *G01K 1/02* (2013.01); *G01N 21/05* (2013.01); *G01N 21/59* (2013.01); *G01N 21/85* (2013.01); *G06K 9/0063* (2013.01); *G08B 21/182* (2013.01); *G01N 2201/061* (2013.01); *G05D 7/0635* (2013.01); *Y10S 901/09* (2013.01)

(56) References Cited

U.S. PATENT DOCUMENTS

| | | | |
|---|---|---|---|
| 6,197,538 B1 | 3/2001 | Van den Berg | |
| 6,571,731 B1* | 6/2003 | Maier, Jr. ................ | A01J 5/007 |
| | | | 119/14.08 |
| 6,742,474 B2* | 6/2004 | van den Berg ....... | A01J 5/0175 |
| | | | 119/14.08 |
| 7,059,766 B2 | 6/2006 | Lemoine | |
| 7,236,237 B2 | 6/2007 | Schmilovitch | |
| 2003/0226510 A1* | 12/2003 | van den Berg ....... | A01J 5/0133 |
| | | | 119/14.02 |
| 2007/0289536 A1 | 12/2007 | Dunn et al. | |
| 2009/0145362 A1* | 6/2009 | Eriksson ................ | A01J 5/0131 |
| | | | 119/14.02 |
| 2011/0017323 A1 | 1/2011 | Herbst | |
| 2012/0097107 A1 | 4/2012 | Torgerson | |
| 2013/0019806 A1* | 1/2013 | De Groot .................. | A01J 5/01 |
| | | | 119/14.02 |
| 2013/0340682 A1 | 12/2013 | Bareket | |
| 2015/0146194 A1 | 5/2015 | Schonrock | |

FOREIGN PATENT DOCUMENTS

| | | |
|---|---|---|
| DE | 102005016412 | 10/2006 |
| EP | 1000535 | 5/2000 |
| EP | 1943897 | 7/2008 |
| SU | 1509005 | 9/1989 |
| SU | 1671202 | 8/1991 |
| WO | 01/09170 | 2/2001 |
| WO | 2005093387 | 10/2005 |
| WO | 2008093344 | 8/2008 |

OTHER PUBLICATIONS

International Search Report for PCT/NL2012/050475 issued on Nov. 12, 2012.
Search Report for priority document NL2007149 including English Written Opinion issued on Apr. 27, 2012.

* cited by examiner

DETECTOR SYSTEM, SENSOR AND DAIRY ANIMAL TREATMENT DEVICE

CROSS REFERENCE TO RELATED APPLICATIONS

This application is a divisional of U.S. Ser. No. 14/158,900 filed on 20 Jan. 2014, allowed, which is a continuation of PCT application number PCT/NL2012/050475 filed on 5 Jul. 2012, and claims the benefit of priority from Netherlands application number 2007149 filed on 20 Jul. 2011. The contents of each of these applications are hereby incorporated by reference in their entireties.

BACKGROUND OF THE INVENTION

1. Field of the Invention

The invention relates generally to a sensor system with a sensor device comprising a through-flow cell having a liquid supply opening and a liquid discharge opening, which through-flow cell is configured to allow a liquid to flow through it, a detector device which is configured to measure a property of the liquid in the cell and to generate an associated detector signal, and a sensor control which is configured to analyze the detector signal.

2. Description of the Related Art

Such sensor systems are generally known per se. They are used, for example, during milking for determining the properties of the milk which has been obtained, in order to carry out quality measurement. To this end, reference is made, for example, to DE 27 59 126, which teaches to separate off milk if a different colour is detected, and to allow it to flow back to the main tank once the flow of milk displays the "correct" colour again. EP1000535 discloses a method for monitoring the quality of milk by shining light of various colours through it and evaluating the relative transmission.

It is a drawback of the abovementioned systems that they do not ensure a correct evaluation of the liquid under all circumstances.

BRIEF SUMMARY OF THE INVENTION

It is an object of the invention to improve the system of the kind mentioned in the preamble, in particular to provide an additional or alternative system which can detect changes in the liquid under more, or at least different, circumstances with a high degree of reliability.

The abovementioned object is achieved by providing a sensor system with a sensor device comprising a through-flow cell having a liquid supply opening and a liquid discharge opening, which through-flow cell is configured to allow a liquid to flow through it, a detector device which is configured to measure a property of the liquid in the cell and to generate an associated detector signal, a sensor control which is configured to analyze the detector signal, wherein the sensor control is configured to detect a liquid transition between two different liquids in the through-flow cell when a change in the detector signal per unit time and/or a change in the detector signal is greater than a predetermined change threshold value or than a predetermined threshold value, respectively, wherein the sensor control is configured to generate an alarm signal if the sensor control detects such a liquid transition.

The invention is based on the insight that, if a change in the liquid occurs, it is always possible to detect a transition in between. Thus, a liquid transition generally takes place where that property changes, either permanently or temporarily, such as a colour, conductivity, etc. It should be noted that the known systems generally compare a parameter value to an absolute value. As a result thereof, gradual changes, which nevertheless result in changes in the measured parameter value with one and the same liquid, could lead to false-positive alarm signals. The present invention limits these false-positive signals by considering the degree and/or velocity of the change of said parameter value.

By generating an alarm signal when detecting a liquid transition, a control system or operator can, if desired, take action, for example if such a transition should not occur according to the actions which have already been carried out. As an example, which will be explained in more detail later, the supply of liquid for a specific treatment, in particular of an animal, may be mentioned, in which an alarm is triggered if a liquid transition is detected. It is, possible that the wrong liquid is accidentally supplied which could have undesirable, health-threatening consequences. It is also possible to reduce risks of damage or incorrect treatment of machines and other products.

In an embodiment, a liquid presence detection mechanism is configured to emit a liquid presence signal if liquid is present in the cell.

In a further embodiment, the sensor control is configured to ignore the detector signal if there is no liquid presence signal.

In another embodiment, the change comprises at least one peak or trough in the detector signal, wherein the peak or the trough has at least a predetermined magnitude.

In an embodiment, the peak and/or the trough has a maximum predetermined length or time duration.

According to a further embodiment, the change threshold value and/or the threshold value are/is a function of the detector signal during a predetermined time period, In a further embodiment, the change threshold value and/or the threshold value are/is a function of the variance in and/or the standard deviation or maximum change of the detector signal during said time period.

In another embodiment, the property of the liquid to be measured comprises an optical property of the liquid.

In a further embodiment, the sensor system further comprises a light source which is configured to pass optical radiation through the through-flow cell, wherein the detector comprises an optical detector which is configured to pick up and detect the emitted optical radiation which has passed through the liquid, and advantageously comprises several light-sensitive detectors, more advantageously a CCD or CMOS device, yet more advantageously an RGB chip.

In another embodiment, the property of the liquid to be measured is at least one of absorption of the optical radiation, refraction of the optical radiation, diffusion of the optical radiation and reflection of the optical radiation.

In an embodiment, the light source comprises several partial light sources which emit optical radiation of different wavelengths.

In a further embodiment, the light source and/or at least one partial light source and/or at least one optical detector is provided in the through-flow cell.

In an embodiment, the light source and/or at least one partial light source and/or at least one optical detector is provided around the through-flow cell, and the through-flow cell is translucent or transparent at least at the location of said light source or said at least one partial light source.

In another embodiment, the light source or at least one partial light source is configured to emit a light beam, and the detector is arranged and configured to detect the emitted light beam which has passed through the through-flow cell.

In a further embodiment, the sensor control is configured to detect a liquid transition if the detector signal changes by more than a predetermined threshold change within a predetermined time period.

In another embodiment, a velocity indicator is configured to provide a liquid velocity signal to the sensor control which indicates a velocity of the liquid in the through-flow cell, and the predetermined time period is dependent on the liquid velocity.

In a further embodiment, the light source is configured to emit a light beam through the through-flow cell, and the device comprises an optical sensor which is configured to detect a detection position on the optical sensor of the light beam which has passed through the through-flow cell.

In an embodiment the measured property comprises the detection position.

In another embodiment, the measured property comprises the change in the detection position.

In a further embodiment, the optical detector comprises an image recorder, such as a video camera, which is configured to record an image of the liquid in the through-flow cell, and the sensor control comprises image-processing software to process the image and is configured to detect a liquid transition if the image shows a predetermined minimum change in time.

In another embodiment, the sensor system comprises a gas bubble-suppressing device which is arranged, viewed in the direction of flow, upstream of the through-flow cell.

In a further embodiment, the sensor system comprises a gas bubble-suppressing device having a portion which has a larger cross-section than the liquid supply opening.

In an embodiment, the portion of the gas bubble-suppressing device having a larger cross-section than the liquid supply opening extends underneath the liquid opening.

In an embodiment, the detector comprises a temperature sensor which is configured to measure the temperature of the liquid in the through-flow cell.

In another embodiment, the measured property comprises the temperature of the liquid.

In a further embodiment, the sensor control is configured to generate an alarm signal if the temperature changes by more than a change threshold.

In another embodiment, the sensor control is configured to generate an alarm signal if the temperature changes by more than a change threshold within a predetermined time period.

In a further embodiment, the sensor control is configured to generate an alarm signal if the temperature changes by more than a change threshold within a time period depending on the liquid flow velocity.

In an embodiment, the sensor control is configured to generate an alarm signal if, within a predetermined time period the temperature shows a peak of at least a predetermined magnitude, followed by a decrease by at least a predetermined decrease threshold.

In an embodiment, the sensor control is configured to generate an alarm signal if, within a time period depending on the liquid flow velocity, the temperature shows a peak of at least a predetermined magnitude.

In a further embodiment, the sensor control is configured to generate an alarm signal if, within a time period, or within a time period depending on the liquid flow velocity, the temperature shows an increase by at least a predetermined increase threshold followed by a decrease by at least a predetermined decrease threshold.

The invention also relates to a sensor device which is suitable for use in the sensor system according to the invention, comprising a through-flow cell having a liquid supply opening and a liquid discharge opening, which through-flow cell is configured to allow a liquid to flow through it, a detector device which is configured to measure a property of the liquid in the cell and to generate an associated detector signal respectively, a sensor control which is configured to analyze the detector signal, the through-flow cell comprising a tube made of light-emitting material, and the detector device comprising several light sources and several light-sensitive sensors which are arranged around the through-flow cell.

In an embodiment, the detector device is configured to measure several properties and generates several associated detector signals.

In an embodiment, the sensor is configured to sense at least one of an optical property, an optical radiation, a refraction of an optical radiation, a diffusion of an optical radiation, a reflection of an optical radiation, a liquid velocity, an emitted beam passing through the though-flow cell, and a temperature.

In an embodiment, a metal hose nipple is provided on each of the two ends of the through-flow cell, and a conductivity and/or impedance meter is connected to the hose nipples.

In an further embodiment, a dairy animal treatment device is provided, comprising a teat detection device for detecting the teats of a dairy animal, a teat treatment device for carrying out a teat-related operation on the teat, a robot arm with a control device configured to operatively bring the teat treatment device to at least one of the teats by means of the teat detection device, and the dairy animal treatment device further comprises at least one liquid line, and a sensor system, wherein at least the through-flow cell can be brought into liquid communication with the liquid line.

In an embodiment, the through-flow cell can be connected to the liquid line.

In another embodiment, the liquid line comprises a teat treatment liquid supply line and the dairy animal treatment device is configured to add teat treatment liquid for the teat treatment.

In an embodiment, the liquid line comprises a teat treatment liquid supply line and wherein the dairy animal treatment device is configured to apply the teat treatment liquid to the teat, via the teat treatment liquid supply line.

In an embodiment, the liquid line comprises a teat treatment liquid supply line and the dairy animal treatment device is configured to apply the teat treatment liquid to the teat via the teat treatment device.

In a further embodiment, a storage container for teat treatment liquid is provided which is connected to the liquid line so as to be closable by a controllable valve, and the control device is configured to make the controllable valve close the connection between the storage container and the liquid line on the basis of a generated alarm signal.

In another embodiment, the teat treatment device comprises a teat-cleaning device and/or a teat aftertreatment device.

All particular features which have been mentioned in connection with the sensor device, in principle, apply equally to the sensor system, and vice versa, unless the text specifically states the opposite.

In particular, the sensor device comprises a liquid presence detection mechanism which is configured to emit a liquid presence signal if liquid is present in the through-flow cell. Such a liquid presence detection mechanism prevents a signal which is measured by the detector during transition to absence of a liquid from being regarded as a liquid transition signal, since this would, in many cases, generate an unwarranted alarm signal. A liquid detection mechanism is, for example, based on measuring an electrical conductivity in the through-flow cell. The reason for this is that, in general, liquids have a much greater conductivity than air. As soon as there is no longer any liquid present, the measured conductivity will drop considerably to below a broadly selectable threshold. An accurate determination is therefore not necessary. Another possibility is, for example, a weight sensor in the cell or an optical detector of a level of liquid or the like. Reference is made to the prior art for alternatives which are known per se.

It should be noted that, in some cases, it may be useful to cause the absence of liquid to generate an alarm, for example if liquid always has to be present. Consideration may be given, for example, to engine oil in an engine. In an embodiment, however, the sensor control is configured to disregard the detector signal when the liquid presence signal is absent. In this way, it is ensured that the substances which are compared are indeed liquids.

In embodiments, the change comprises at least one peak or trough in the detector signal, wherein the peak or the trough has at least a predetermined magnitude. In this case, a peak is, as usual, characterized by an increase, followed by a decrease, and a trough is characterized by a decrease followed by an increase. When the smallest of a decrease and an associated increase at least has the predetermined magnitude, the associated trough or the peak at least has said predetermined magnitude. Cases where only the decrease or the increase achieves said magnitude indicate a stage, rather than a peak or trough. The predetermined magnitude may, for example, be chosen on the basis of practical tests and, in virtually all cases, depends on the actual parameter to be measured. Thus, a noisy parameter will lead to a relatively large predetermined magnitude for a meaningful peak/through. Otherwise, a meaningless noise ripple would lead to a false-positive liquid transition detection. On the other hand, if the value were excessive, a small peak/through in a parameter which, for the remainder, does not vary, or varies only very slowly, could be unjustly overlooked (false-negative). The person skilled in the art can easily determine such suitable magnitudes in practice, after choosing the parameter(s). This choice depends to a certain degree on the desire not to generate too many false-positives (too sensitive) or, on the contrary, too many false-negatives (too insensitive).

When such a peak or trough is detected, this is very likely the result of a boundary surface between two liquids, and thus a transition from one liquid to the other. After all, such a transition is often not only characterized by a change in stable values of a variable, such as colour, conductivity, which depend on the intrinsic properties of the respective liquids, but also on any consequences of reactions and the like at the boundary surface between two liquids. This boundary surface, or rather boundary region, can then differ from both the first and the second liquid.

In particular, the peak and/or the trough has a maximum predetermined length or time duration. This measure serves to prevent significant, but very slow changes, such as those caused, for example, by gradual heating and cooling down of the liquid, e.g. in the daily temperature variation, being regarded as a liquid transition. The predetermined length (or in many cases time period) can he chosen on the basis of the embodiment of the sensor device. It may, for example, be between a few tenths of a second to approximately five seconds. Some variables which can be taken into account are:

the mean flow velocity to be expected. At a greater velocity, the boundary or liquid transition region will also pass more quickly. The length/time period may be shorter;

the distance of a liquid source to the sensor. With a relatively great distance, a larger degree of mixing between the boundary region and the respective liquids may occur, and any peak/through will widen. The length/time period has to be longer;

the speed of the detector device, which has to be sufficiently quick to measure a passing liquid transition.

the thickness of the liquid line/the through-flow cell. The thinner the line or cell, the more difficult it is for mixture to occur. The length/time period may be shorter.

It should be noted that detecting a peak or trough, i.e. a temporary, relatively large and rapid change, in a parameter may well indicate a boundary region or liquid transition. Often, this is more unequivocal than a gradual change. After all, if only the fact whether or not a threshold value is exceeded in an absolute sense is being considered, this gradual change in value may be caused in the intrinsic liquid, for example by mechanisms such as heating up or ageing. Even in those cases, it will often or virtually always be possible to point out a certain boundary region in which a parameter value has a peak or trough. Therefore it is, in a general sense, advantageous if the sensor device is configured to detect a liquid transition when a change per unit time of the detector signal is greater than a predetermined change threshold value. If, in addition, the value of the parameter itself changes by more than a threshold value, this is an even clearer indication of a liquid transition. It is therefore even more advantageous if the sensor device is configured to detect a liquid transition when, in addition, a change in the detector signal exceeds a predetermined threshold value. In addition, a still more accurate detection may be achieved if an absolute value of the parameter is exceeded. It is therefore even more advantageous if the sensor device is configured to detect a liquid transition when the detector signal, in addition, exceeds a predetermined absolute value.

In particular, the change threshold value and/or the threshold value are/is a function of the detector signal during a predetermined time period. Thus, the (change) threshold value can, if desired, be adjusted in a dynamic manner to the value of the detector signal, in order to be able, for example, to take into account a drift or the like which is meaningless for the detection per se. More particularly, the change threshold value and/or the threshold value are/is a function of the variance in and/or the standard deviation or maximum change of the detector signal during said time period.

In embodiments, the property comprises an optical property of the liquid. An advantage of choosing an optical property is the fact that this can in many cases be determined very quickly and accurately, and, in addition, usually non-invasively, that is to say without affecting the liquid, or only to a very small degree.

In embodiments, the sensor system, or the sensor device, comprises a light source which is configured to pass optical radiation through the through-flow cell, wherein the detector comprises an optical detector which is configured to pick up and detect the emitted optical radiation which has passed through the liquid. By using light in this way, the above-mentioned advantages of using an optical property with accurate and quick measurement can be achieved. Preferably, the light source is configured to emit the optical radiation in a beam. This not only facilitates the manipulation of the optical radiation, but also limits the area which interacts with the liquid. Another important advantage is the fact that the region of interaction can be chosen, for example in the bottom of the through-flow cell, where liquid will be present most often. Advantageously, the detector comprises several optical detectors, more advantageously a CCD or CMOS device, yet more advantageously an RGB chip. Thus, a relatively inexpensive detector is provided which can pick up several signals simultaneously, not only of different wavelengths, i.e. red, green and blue, but, if desired, also from different angles, in particular if the chip is relatively large.

In particular, the property is at least one of absorption of the optical radiation, refraction of the optical radiation, diffusion of the optical radiation and reflection of the optical radiation. All these variables, and in particular also a combination thereof, may form useful parameters for detecting a liquid transition. Thus, the absorption of one liquid may be much greater or smaller than that of the other, leading to a significant change in the signal at the liquid transition. It is also possible, in the case of mutually reactive liquids, for a chemical reaction to occur which leads to turbidity or precipitation by reaction products. In this case, even with intrinsically clear liquids, a peak signal could occur in the absorption, as may be the case for the diffusion as well. Precipitation may also be present, for example due to sediment or the like being suctioned from the bottom of the vessel. Whether it is sediment or a chemical precipitate, in both cases an alarm signal is generated. It is also possible, even with intrinsically clear liquids, for the refractive index to differ, which can relatively easily be determined using an optical radiation beam. Based on the above, the person skilled in the art can readily deduce other possibilities or combinations. Furthermore, equivalent or complementary variables, such as transmission in case of absorption, are covered by the scope of the disclosure.

In embodiments, the light source comprises several partial light sources which emit optical radiation of different wavelengths. Thus, it is alternatively or additionally possible to measure one, or advantageously, more parameter values for different wavelengths, so that more information about the liquid and transitions therein can be obtained. In this context, "different" is in particular understood to mean that the wavelength ranges do not overlap within Full Width at Half Maximum (FWHM). Advantageously, at least a part of the light sources is monochromatic, in particular having a wavelength range of at most 50 nm, such as LEDs or laser lights. In the case of overlapping wavelength regions, undesired signal overlap may be prevented by alternate driving. Alternatively, one or more partial light sources may emit broadband radiation, such as "white" light, in which case, for example, one or more sensors are provided with a filter in order to make a selection of the radiation.

In embodiments, it is possible to measure the change in value of at least one key parameter before and after a period of instability as a detector signal to determine a liquid transition. When the change in value exceeds a positive or negative threshold, it is assumed that a liquid transition has occurred. In this case, the period of instability is defined as the period in which a change in at least one instability-monitoring parameter exceeds an instability threshold. In this case, change may again comprise "absolute change in value", optionally per unit time, "relative change in value" optionally per unit time, absolute or relative standard deviation during a predetermined sampling period etc. The instability parameter(s) may in this case be identical to or overlap the main parameter(s), or may also comprise at least one other parameter. The understanding underlying these embodiments is the fact that one parameter is very suitable as an indication that a change may be occurring, i.e. acts as an alert (the instability-monitoring parameter), while another parameter can give more precise information about the type of liquid(s), e.g. to assess whether truly distinctly different liquids can be detected before and after the phase of instability. After all, it is possible that a new batch of the same liquid is being supplied. There may then indeed be a difference in the liquid due to a difference in temperature, ageing, difference in concentration or the like, i.e. a liquid transition, but it may not be substantial. Making use of a parameter which is more relevant to this determination then helps to prevent false alarms from being raised. For example, the ratio between the measured optical radiation at two (or more) wavelengths is chosen as the instability-monitoring parameter, and the total intensity value at said wavelengths and/or even across the entire spectrum is chosen as the main parameter. In this case, the period of instability starts or ends, respectively, when the (absolute or preferably relative) standard deviation in said ratio (if desired in the sum of the ratio at different pairs of wavelengths) rises above a threshold and then drops below the latter again. The main parameter value(s) measured directly prior to the period of instability then forms the initial value, and the main parameter value(s) measured directly after the phase of instability then forms the final value. Only if the final value(s) and the initial value(s) differ from one another by more than a change threshold, is the actual assumption made that liquid transition has occurred. The choice of, in this case, the colour ratio is based on the fact that, as the inventors have found, air bubbles only have little influence on the colour ratio, but a large influence on the intensity value. As a result thereof, air bubbles which are carried along will not result in a period of instability, as occurs with, for example, an actual liquid transition, but actual changes in the colour ratio will. These embodiments ensure that there will not be too many instances when a period of instability is detected which is not an actual liquid transition. This not only saves computing power, but also reduces the risk of false alarms. Incidentally, this method of determining a liquid transition can still be used in parallel with/in addition to other method(s), or rather as an additional criterion.

In particular, the light source and/or at least one partial light source and/or at least one optical detector is provided in the cell. This prevents the optical radiation from being affected by the wall of the cell, for example by scratching or discolouration.

Alternatively or additionally, the light source and/or at least one partial light source and/or at least one optical detector is provided around the cell, in which case the cell is translucent or transparent, at least at the location of said light source or partial light source. Thus the (partial) light source cannot be influenced by the liquid which is a significant advantage, for example in the case of aggressive liquids. In addition, this makes it easier for the (partial) light source to be replaced, repaired or the like. If desired, the translucent or transparent part of the cell at the location of the (partial) light source or optical detector may be formed by a window which may be made from a suitable material which, for example, is compatible with the liquid. The cell may also be entirely made from such material, such as a tube of light-emitting material, such as polysulfone or polycarbonate, or preferably from a glass, such as borosilicate glass, for high scratch and chemical resistance.

Advantageously, if the through-flow cell is cylindrical and made from light-emitting material and the (partial) light source is arranged outside the through-flow cell, the optical detector is arranged in the path of the emitted light beam and the emission angle of the beam of the light source, the refractive index of the light-emitting material of the through-flow cell and the cross section of the through-flow cell are adapted to one another in such a manner that if the through-flow cell is filled with a desired liquid, at least half, and preferably substantially all, of the emitted beam lands on the optical detector, while, if no liquid is present in the through-flow cell, less than half, preferably at most rounded to 0.2 part of the beam lands on the optical detector. The figures given here apply to the non-absorbed and non-diffused part of the beam. Said measure offers the advantage that the presence of liquid, and in particular of the desired liquid, can be shown in a very simple manner. The liquid in the cell then acts as a convex lens which directs the beam onto the opposite detector. Without liquid, the beam will continue to diffuse. This causes a (very) significant brightness difference between a cell with liquid and a cell without liquid. Even with absorbing, but not extremely absorbing liquids, the signal with liquid may still be stronger than that without liquid. Therefore, such an arrangement may also serve as a liquid presence detector.

In an embodiment, the light source or at least one partial light source is configured to emit a light beam, and the detector is arranged and configured to detect the emitted beam which has passed through the through-flow cell. If the radiation is emitted in the form of a beam, it is possible, as has been indicated above for the light source in general, to manipulate the optical radiation, but also to limit the region which interacts with the liquid, if desired differently for each partial light source. Yet another important advantage is the fact that the region of interaction can be selected, for example at the bottom of the through-flow cell, where liquid will be present most often. Advantageously, there are several, for example two, three or four, partial light sources, each of which emits a light beam, and there are several detectors, such as two, three or four, to detect the plurality of light beams. The partial light sources may comprise light of a limited wavelength range (monochromatic or narrow-band light). They may also, and even advantageously, emit white light or broad-band light, including, if desired, (near) infrared. The detectors may correspondingly be sensitive to monochromatic, narrow-band or broadband light, such as the part sensors of an RGB sensor. This sensitivity may be intrinsic, or may also be caused by filtering of the light which is incident on the sensor. Thus, due to the particularly high luminosity which can be achieved with white light in particular and which is moreover available for many different properties and sensors, different effects, such as transmission, reflection and absorption, can be detected and measured for different circumstances, such as for different angles, distance through the liquid, different wavelength, etc, and in particular also for combinations of these properties. It is this last property, the ability to measure several properties simultaneously, which is a significant advantage of the present sensor system, as it is thus possible to detect a liquid transition in a more reliable manner. It will always be possible to detect a liquid transition, in particular one from a desired and known liquid to any other, undesired liquid, if it is known beforehand which property changes. But this is exactly what cannot be predicted. For this reason, the present system can measure a plurality of properties, so that a clear change in a property, and better still, a significant and simultaneous change in at least two properties, can indicate a transition to another, undesired liquid in a reliable manner.

Thus, in an embodiment, the sensor system comprises a conductivity or impedance meter for measuring the conductivity or impedance of the liquid in the cell. Conductivity is a valuable parameter for characterizing liquids. Very advantageously, the through-flow cell comprises a hose nipple at each of its ends. These are intended for connecting the cell to a supply and a discharge line. In this case, the hose nipples are advantageously configured as electrodes for the conductivity or impedance meter. This has the considerable advantage that no separate fed-through electrodes are required in the through-flow cell, so that no leaks are being caused. In addition, the manufacture thereof is much simpler. Moreover, a larger electrode surface is available, so that the measurement is much less sensitive to air bubbles, contamination and the like. Also, the electrodes do not protrude into the path of the liquid, so that the flow thereof is affected as little as possible. All this does however require an electrical insulation between the hose nipples. This may be provided by insulating material between the hose nipples and the through-flow cell and/or a through-flow cell which is itself made of insulating material, such as plastic or, preferably, a glass.

Advantageously, the sensor control is configured to detect a liquid transition if the detector signal changes by more than a predetermined threshold change within a predetermined time period. As has already been indicated earlier, with a sufficiently large change, in particular per unit time, of one of more measured variables, it is very likely that there is a liquid transition, and in any case sufficiently likely to warrant an alarm signal.

Embodiments may comprise a velocity indicator which is configured to provide a liquid velocity signal to the sensor control velocity which indicates a velocity of the liquid in the through-flow cell, wherein the predetermined time period is dependent on the liquid velocity. Thus, the sensor device can efficiently take the speed at which the liquid flows through the cell into account. After all, if the liquid flows, for example, very slowly, even a gradual change in the signal may already be a reason for an alarm signal, whereas if the liquid flows very quickly, a short peak in the signal may mean more than just an accidental noise ripple. Taking into account the liquid flow velocity assists in correctly interpreting the measured values and changes.

In an alternative or additional measure, the light source is configured to emit a light beam through the through-flow cell, in which case the device comprises an optical sensor which is configured to detect a detection position on the optical sensor of the light beam which has passed through the through-flow cell. Advantageously, the property comprises the detection position, in particular a change in said detection position. Alternatively or additionally, the property comprises the magnitude or change in magnitude of a beam on the detector, which may in itself consist of changes in position of the extremes of the beam. These embodiments are based on the finding that when the liquid remains the same, the position which such a light beam passing through the liquid assumes on the detector will also remain the same. If the liquid changes, this will become evident, for example, by a different refractive index, and thus a different position on the sensor. It should be noted that this will be the case in particular for a beam passing through the liquid at an angle, in which case the angle of refraction of entrance will change. If a very inclined angle of incidence is selected, advantageously of 60° or more with respect to the normal, on the liquid body, or the through-flow cell at the location where the light enters, even a small change in the refractive index will cause a relatively large change in position. Equally, a very inclined, preferably substantially grazing, incidence of light on the optical sensor will cause a small change in the refractive index to result in a large change in position. In this case, in this application, a very inclined angle of incidence is an angle of less than 30° to the sensor surface, and a substantially grazing angle of incidence is an angle of at most 10° to the sensor surface, in which case, however, other angles are certainly not excluded. It should be noted that such an optical sensor may also act as a liquid presence detector, as the position of the beam from refraction by air will be completely different to that from refraction by any liquid in the cell. Furthermore, the sensor system or the corresponding sensor device may be used as an accurate absolute determiner of the refractive index.

In particular, a transition is characterized by (mixing) vortices and/or a local temperature increase. The abovementioned change in position in particular relates to a more or less stable beam position before and after passing of a liquid transition. As has already been indicated above, it is also possible for a reaction to take place at the boundary surface of two different liquids, resulting in different substances which may, only locally cause a different refractive index. Thus, even if two different liquids have the same refractive index, it is still possible that this is no longer the case in their boundary region. A temporary change of the detection position is then still a reliable indicator of a liquid transition. Therefore, it is possible that a time-related change threshold may also be relevant to the change in position: when it is exceeded, it is highly likely that a liquid transition has been detected. The sensor control may then be configured accordingly to detect the latter.

Another reason why a temporary change in the detection position on the optical sensor may also be important, is that the beam may be reflected at the boundary surface between two liquids, again due to differences in the refractive index. In theory, and in the simplest approach, said boundary surface is a perpendicular plane to the wall of the through-flow cell with non-mixing and non-reacting liquids. It should be noted that it is advantageous in this case to have a light beam which does strike the liquid at an angle, but rather at a larger angle to the normal, that is to say at a small angle, and preferably grazing, with respect to said boundary surface. As a result, a small difference in refractive index will still cause a large reflection. However, in practice, the boundary surface will often consist of vortices. In this case, a relatively anomalous position signal will be detected on the optical sensor with each beam direction. Preferably, the sensor control is therefore configured to detect the time change of the detected position on the optical sensor, advantageously in order to detect a liquid transition if said time change exceeds a predetermined threshold. It should be noted that the time change in this case is preferably seen as a cumulative sum of the absolute changes, in other words a change to and fro is counted as ABS(change to)+ABS (change fro). Nevertheless, it would also be possible to detect the maximum change in position, such as for example an amplitude of a periodic change, as liquid transition.

Particular embodiments of the sensor system or the sensor device are characterized by the fact that it comprises an image recorder, such as a video camera, which is configured to record an image of the liquid in the through-flow cell, and wherein the sensor control comprises image-processing software to process the image and is configured to detect a liquid transition if the image shows a predetermined minimum change in time. The image recorded by the image recorder, such as a CCD or CMOS camera, which obviously has to be a dynamic image or at least a repeatedly recorded image, is in this case analyzed by the image-processing software. The latter compares the images to one another, either by comparing successive images or by comparing each new image to a specific standard, such as a moving average of the past x images, and determines the degree of change therein. The latter comprises, for example, the change in image information per pixel, summed up for the pixels of the image. In theory, with a completely homogeneous liquid, no change will occur, whereas, if a boundary surface flows past, a very substantial change will occur in the image. It should be noted that in particular the beam which is visible in the image, and the brightness, position and colour thereof, will determine a large part of the image information. Refraction, colour change, local turbidity due to reaction products, vortices etc. will all affect said image information. In particular optical techniques will be able to provide greater sensitivity and reliability.

Advantageously, the device comprises a gas bubble-suppressing device which is arranged, viewed in the direction of flow, upstream of the through-flow cell. This gas bubble-suppressing device serves to prevent false-positive detections due to gas bubbles as much as possible. After all, a liquid/gas bubble transition is a transition which results in a clear signal, but which does not indicate a liquid transition. The refractive index of gas is always lower than that of liquid, and therefore, reflection on the gas bubble is also always possible.

The gas bubble-suppressing device is not limited in any particular way, and may, for example, comprise a bubble-capturing device, such as bristles or gauze. Advantageously, the through-flow cell comprises a section having a larger cross section than the liquid supply opening. In this way, the liquid can come to rest to some extent in this wider, thicker section in order to allow any gas bubbles to rise, in some cases even to the surface. The combination then advantageously is a kind of air-liquid separator. In particular, this section extends underneath the liquid opening, thus enabling it to fulfil its purpose in the liquid stream as early as possible.

In advantageous embodiments, the detector comprises a temperature sensor which is configured to measure the temperature of the liquid in the through-flow cell. This may be advantageous, for example, in order to be able to carry out possible temperature correction on the measured values. Thus, almost any variable could be slightly temperature-dependent, such as the refractive index (and consequently also the beam detection position on an optical sensor), absorption etc. By then being able to correct for the temperature, it is possible to prevent any false-positive liquid transition detection. For example, if the outside temperature increases, the temperature of the liquid could also increase, which does not, however, have to have any relevant meaning for the liquid.

In embodiments, the property comprises the temperature of the liquid. After all, it could be the case that instead of a liquid with a desired temperature, such as in particular at or slightly below body temperature, a much colder or hotter liquid is supplied. This could lead to discomfort or even danger when treating animals and the like. Since the temperature difference between the first and second liquid will be maintained if the supply lines are not excessively long, except for a transition in the boundary region, an alarm signal will be generated correctly in the case of an increase or decrease by more than a change threshold, in particular if the change by more than a change threshold occurs within a predetermined time period, more particularly within a time period which depends on the liquid flow velocity. Thus, it is possible to take into account the length, and any insulation, of the supply line, and the supply velocity of the liquid.

In embodiments, the sensor system comprises a flow-disturbing element which is arranged, viewed in the direction of flow, upstream of the detector. The flow-disturbing element which, for example, protrudes into the through-flow cell or a liquid-supplying line will generate vortices in the liquid flowing past. With a homogenous liquid, these will hardly be detectable, if at all. However, if a liquid transition is present, these vortices will ensure that the transition extends across a larger volume, and is thus visible for longer and/or more visible for the detector(s). A flow-disturbing element may be, for example, a pin which is specifically fitted for this purpose or, for example, also an electrode or sensor for conductivity/impedance or temperature or the like which already projected into the liquid path.

In particularly advantageous embodiments, the sensor control is configured to generate an alarm signal if the temperature shows a peak of at least a predetermined magnitude within a predetermined time period, more particularly within a time period depending on the liquid flow velocity. These important embodiments are based on the insight that a reaction occurring during a liquid transition, in the boundary region between the two liquids, may often also cause a local increase in temperature. The heat of reaction may stem from a chemical reaction, but, for example, also from mixing or dissolving one liquid into the other.

Even if the first and second liquid have the same temperature, such a peak may occur in between which is indicative of a liquid transition. In practice, the first and second liquid will not always have the same (base) temperature. Nevertheless, the term "peak" is in particular understood to mean that, and the sensor control is configured to generate an alarm signal if, the temperature shows an increase by at least a predetermined increase threshold, followed by a decrease by at least a predetermined decrease threshold. The increase and decrease threshold do not have to be identical. Nevertheless, it is clear that the boundary region is then hotter than both the first and the second liquid. This is a clear indication of a reaction between the two liquids, which is almost always undesirable, and anyhow indicates that there is a liquid transition. The increase and decrease threshold may each, for example, have a value of between 1 and 5° C. The possible predetermined time period may have a value of, for example, between 1 and 5 seconds. This means, for example, that a temperature increase of at least 3° C. within 5 seconds, followed by a decrease by at least 2° C. within 5 seconds is sufficiently reliable as an indication of a non-noise-related temperature peak indicating a liquid transition.

It will be clear that, as has already been mentioned above, a combination of a temperature measurement and/or an optical measurement and/or a conductivity/impedance measurement results in an even more reliable liquid transition detection.

As has also already been indicated above, the invention also relates to a sensor device per se. Such a sensor device, and corresponding sensor systems, are eminently suitable to distinguish substances, by determining several properties in combination, such as transmission/absorption (and therefrom optionally colour), diffusion, reflection, refractive index, all for different wavelengths, if desired, and optionally supplemented by temperature, conductivity/impedance, etc. This property of compiling some kind of passport or signature of properties to substances is useful for identifying said substances. It is even useful for identifying air bubbles in liquid. In those cases, there is always a transition from the present liquid to air, with a characterizing transition in the refractive index, reflection etc. When identifying such an air bubble, the sensor system, for example, could decide to ignore such a detected transition as meaningless. Alternatively, detection of an air bubble, and in particular a detection frequency higher than a threshold frequency, could indicate a leak or a disrupted liquid supply. In this case, an alarm signal could also be generated.

Furthermore, it is noted that the provision of several light sources and several detectors, preferably around a space having a round cross section, such as a cylindrical through-flow cell, offers the advantage that many related properties, such as diffusion and reflection, are measured at different angles and/or in different positions. This offers possibilities of calculating the base parameters on the basis of the plurality of detector signals. In those cases where a single detector cannot distinguish the constituent parts of a signal which is, after all, composed of transmission, refraction and one or more reflection signals and one or more diffusion signals, these can be derived by deconvoluting and the like from the plurality of detection signals.

The invention also relates to a dairy animal treatment device, comprising a teat detection device for detecting the teats of a dairy animal, a teat treatment device for carrying out a teat-related operation on the teat, a robot arm with a control device configured to operatively bring the teat treatment device to at least one of the teats by means of the teat detection device, wherein the dairy animal treatment device comprises at least one liquid line, and a sensor device, wherein at least the through-flow cell can be brought into liquid communication with the liquid line, wherein in particular the through-flow cell can be connected to the liquid line. Such a dairy animal treatment device often performs a teat-related operation on each dairy animal in the herd several times a day. In addition, a teat is a very sensitive part of the dairy animal. It is therefore very important that such a treatment be carried out in a very reliable manner, with as little risk of discomfort or even danger as possible by using an incorrect liquid. The use of a sensor device according to the invention with such a dairy animal treatment device is therefore a considerable advantage. The specific advantages mentioned in connection with the embodiments of the sensor device also apply in full to the dairy animal treatment device, and do therefore not have to be repeated. Nevertheless, a few particular embodiments of the dairy animal treatment device will be discussed below.

Advantageously, the liquid line comprises a teat treatment liquid supply line and the dairy animal treatment device is configured to add teat treatment liquid for the teat treatment, more particularly to apply it to the teat, via the teat treatment liquid supply line, in particular via the teat treatment device. With teat treatments, a liquid is often used, and it is very important to prevent the use of incorrect liquids. If a liquid transition is detected, there is a possibility that the second liquid is undesirable. The alarm signal generated will cause the receiver, in many cases the supervisor or the operator, to take corrective measures, and to limit or prevent damage, in particular to the dairy animal.

In embodiments, the device comprises a storage container for teat treatment liquid which is connected to the liquid line so as to be closable by a controllable valve, wherein the control device is configured to make the controllable valve close the connection between the storage container and the liquid line on the basis of the alarm signal generated. It will be clear that closing the liquid supply as soon as a liquid transition is detected, can prevent a great deal of damage, in particular if the valve is situated sufficiently far upstream of any discharge opening. All this will depend on the velocity of the liquid and the speed at which the control device is able to determine a liquid transition, but can easily be adjusted in practice.

In particular, the teat treatment device comprises a teat-cleaning device and/or a teat aftertreatment device. This is a very direct way of carrying out a teat-related treatment which applies either indirectly, or more particularly directly, liquid to the teat. Examples of such treatments are spraying or covering the teat, or cleaning the teats using a brush moistened with liquid. The liquid contains in particular teat-cleaning, teat-disinfecting or teat-caring agent. It will be clear that it is very dangerous for the dairy animal if a teat were to be sprayed with, for example, an aggressive cleaning agent, such as a liquor or acid or other milk line cleaning agent instead of a teat-disinfecting agent.

In a very advantageous embodiment, the teat treatment device comprises a teat cup which can be placed on a teat and a liquid supply to the inside of the teat cup, in particular for teat cleaning or other teat treatments. The sensor device can then determine whether a liquid transition is taking place in the liquid which is being supplied to the teat cup. This may be either for a liquid for teat treatment, or the teat cup is situated on the teat. After all, it is very dangerous if, for example, a cleaning agent is accidentally supplied. Conversely, it is also possible to detect a liquid transition if the teat cup is being cleaned (automatically). After all, a liquid transition may in this case also indicate an incorrect liquid, such as a teat treatment agent instead of a teat-cup cleaning agent. This would not only lead to a waste of agent and a risk of insufficient cleaning, but could also be an indication that an agent has been mistaken for another, possibly leading to unpleasant consequences for a dairy animal. This could be prevented by using the sensor device according to the invention.

The sensor and/or teat treatment device according to the invention preferably forms part of a milking device. Such a milking device may, for example, be an automatic milking device, wherein a robot arm is provided for fitting milking cups on teats of a dairy animal. Such a device offers the advantages of unsupervised milking which are known per se. In such a case, it is advantageous if the reliability and animal safety are increased, as is the case with the sensor and/or teat treatment device according to the invention. However, the devices can also be used in a milking device for manual fitting of milking cups, in which case a teat treatment is carried out. An example of such a device is, for example, the RotaryMATE by Green Source Automation which comprises a robot arm in a milking carrousel with manual cup fitting, which robot arm automatically sprays the teats with a teat treatment agent. Although an operator is present in each case during milking and the other operations, this work is often carried out by untrained people, and the present invention will in particular benefit the monitoring of the spraying process.

BRIEF DESCRIPTION OF THE DRAWINGS

The features and advantages of the invention will be appreciated upon reference to the following drawings, in which.

DESCRIPTION OF ILLUSTRATIVE EMBODIMENTS

The following is a description of certain embodiments of the invention, given by way of example only and with reference to the drawings.

Figure 1:
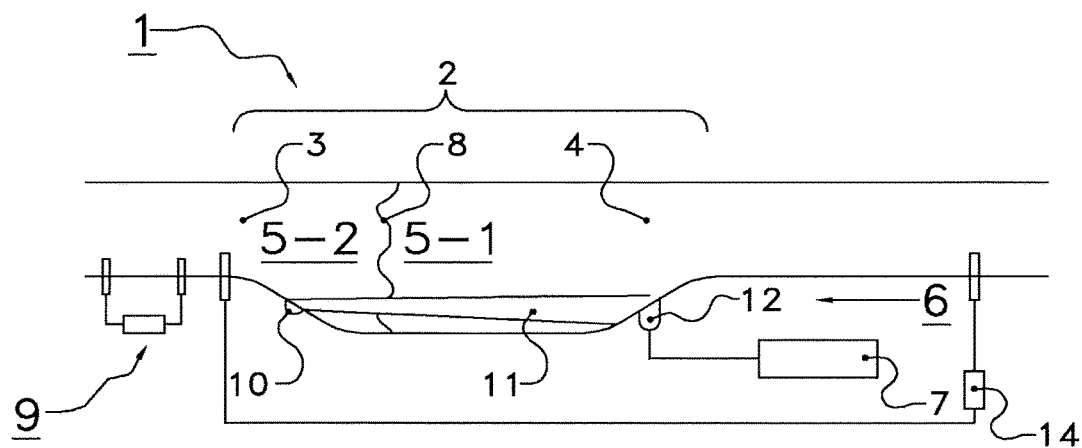
FIG. 1 shows a diagrammatic cross-sectional view of a sensor device according to the invention.

FIG. 1 shows a diagrammatic cross-sectional view of a sensor device 1 according to the invention. Reference numeral 2 denotes a through-flow cell with a liquid supply opening 3 and a liquid discharge opening 4, containing a first liquid 5-1 and a second liquid 5-2 with a boundary surface 8.

A detector device is denoted overall by reference numeral 6, comprising a sensor control 7. Reference numeral 9 denotes an optional liquid presence detector, while reference numeral 10 denotes a light source which emits a light beam 11 to the optical detector 12. Reference numeral 14 denotes an optional conductivity meter.

The through-flow cell 2 has been shown here as forming part of a line through which liquid flows, to the inside via opening 3 and, of course, to the outside via opening 4. The presence of liquid can be detected here by the (optional) liquid presence detector 9, in this case consisting of two electrodes 9a, 9b with a conductivity or resistance meter 9c between them. If liquid is present between the electrodes, the conductivity will be much higher than if this is not the case. Furthermore, in particular the upstream electrode(s) serve(s) as liquid-flow disturbing means or vortex-generating means in order to make vortices on a boundary surface 8 more clearly visible. Incidentally, the detector 9 may also be placed on the upper side of the line in order to ensure that a presence signal is not only generated when there is a thin layer of liquid near the bottom. It should be noted that the presence of liquid can often also be inferred by the measured values of a liquid property from the sensor device 1 itself.

FIG. 1 shows the presence of liquid, namely a first liquid 5-1 and a second liquid 5-2, with a boundary surface 8 in between. In this case, the liquids are non-mixing, such as for example water and oil. In practice, the boundary surface 8 is more likely to be a boundary or transition region in which mixing and/or even a reaction may occur.

It can furthermore be seen that the through-flow cell comprises a lowered and widened section at the bottom, by means of which any gas bubbles present in the liquid, at least those at the bottom, will be removed from the liquid. A light source 10 is also provided there which emits a light beam 11 which is picked up by the optical detector 12 after having passed through the liquid. The light source 10 is, for example, a small light bulb or, preferably, an LED or laser. The light used is, for example, visible or (near) infrared light, although medium or far infrared and UV-light are not ruled out. The light is wide-band or narrow-band light, even up to substantially monochromatic. Preferably, the wavelength or the wavelength region is adapted to the correct liquid to be used. This can also, and advantageously, be a white light source, such as a white light LED, in combination with optical sensors comprising filters or the like which thus have a limited detection range. In this case, an embodiment is characterized by the fact that the type of light used has a most important wavelength which is adapted to the colour of the correct liquid to be used. This is based on the finding that all, at least the majority, of the teat-care liquids have a (visible) colour while all, or at least the majority of, cleaning agents used in practice for milking lines and teat treatment devices are optically colourless. Therefore, when light, for example, of the same colour as the liquid to be used is employed, which will therefore result in a relatively large degree of absorption, a much lower absorption will be measured upon a transition to a colourless liquid. This signal will indicate very clearly that the line does at least no longer contain the correct liquid.

It should be noted that the beam 11 is drawn as a relatively narrow beam. Alternatively, a broad beam may also be emitted or even unbeamed light. This makes an optical detector 12 with a relatively large surface, or several detectors 12 which together cover a relatively large surface, possible. Thus, the signal will average out more and be less sensitive to disturbances caused by, for example, air bubbles.

Incidentally, the detector 12 may be any suitable optical detector, such as photodiodes, light-sensitive resistors, etc. A special optical detector relates to a CCD camera with image-processing software. Such a sensor may then he configured to receive an image of the emitted radiation and to analyze said image. If a boundary surface passes through the image, said image will be deformed. This occurs in particular with liquids of a different colour, brightness, refractive index or the like. The image of the optical radiation or beam will then undergo a relatively large change which can reliably be detected by the sensor control using the image-processing software. Alternatively, such a CCD or CMOS chip can also be used to detect the light, namely in three colours, and optionally also as "clear", that is to say without a colour filter excluding the overall brightness of the signal.

The conductivity meter 14 which is also shown with two illustrated electrodes may, in addition, serve to detect liquid properties since it can detect whether a change in conductivity occurs. For example, this is measured between the electrodes, but preferably, each of the two electrodes is configured to determine the conductivity itself and locally. This is what is referred to as a double conductivity measurement which is slightly shifted in time. This can serve as a more reliable measurement, but also to determine the velocity of the liquid. After all, any variation which is detected by the upstream electrode or other meter, will be detected by the second electrode or other meter some time later. By dividing the distance between the electrodes (or meters) by the time difference, the liquid flow velocity can be determined and the combination thus forms a liquid flow velocity meter. Of course, it is also possible to provide a "dedicated" liquid flow velocity meter which only measures this velocity. In practice, liquid velocities often tend to be in the range of a few centimetres to tens of centimetres per second. The sensor device and the sensor control have to be adapted to such velocities.

Figure 2:
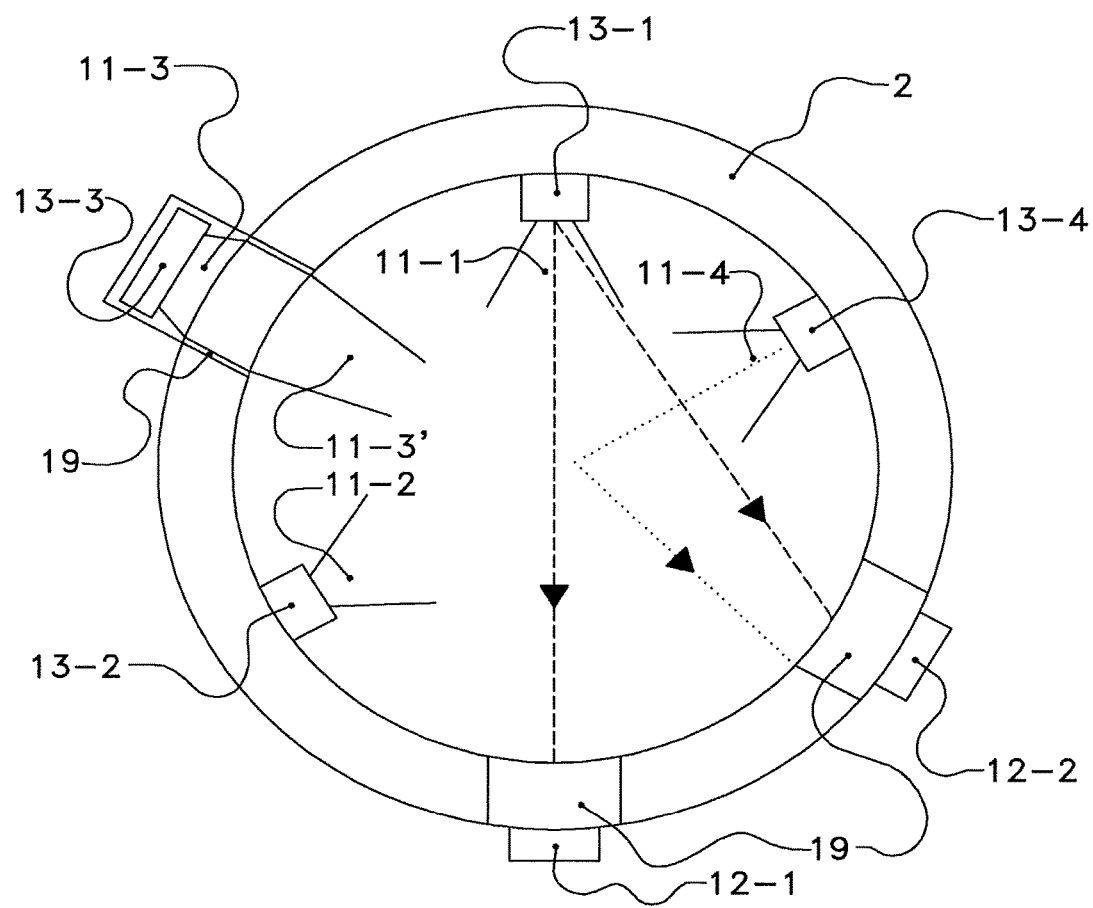
FIG. 2 shows a diagrammatic cross-sectional view of another sensor device according to the invention.

FIG. 2 shows a diagrammatic cross-sectional view of another sensor device according to the invention. It comprises LEDs 13-1, 13-2 and 13-4 arranged on the wall of the through-flow cell, and another LED 13-3 outside the wall, behind transparent windows 19, and two optical detectors 12-1 and 12-2. The LEDs emit respective beams 11-1-11-4.

The illustrated partial light sources 13-1 to 13-4 may, for example, emit different kinds of light, such as white light, red light, green light and blue light. Overlapping wavelength regions are not a problem if the LEDs are actuated alternately. The emitted beams are influenced by the liquid present in the through-flow cell and undergo, for example, absorption, indicated by the straight dashed line in beam 11-1, or diffusion, indicated by the bent dashed line in beam 11-1 and the dotted line in beam 11-4. The respective associated beams are in this example received by optical detectors 12-1 and 12-2, respectively. Of course, more LEDs (partial light sources) and (optical) detectors may be provided. It is important that, with this embodiment, a variety of optical properties of the liquid can be detected for several types of light, and thus also the changes therein. This greatly increases the reliability, partly because properties for several light paths can be determined.

LED 13-3 emits a beam 11-3 which is refracted by the material of the wall of the cell 2 and the liquid in the cell to a converging beam 11-3' which is directed at and converges at detector 12-2 and results in a strong signal. If the liquid were absent, the beam would be wide and result in a much weaker signal.

The illustrated windows 19 are preferably transparent, at least for the radiation emitted by the associated source/LED or for the radiation to be received by the detectors 12-1, 12-2. Alternatively, the entire through-flow cell or even line is transparent to said radiation, such as a through-flow cell made of borosilicate or another type of glass. The use of windows 19 is advantageous if the (partial) light source(s) or optical detector(s) are sensitive to the liquid or for example in order to replace or repair them more easily.

Figure 3:
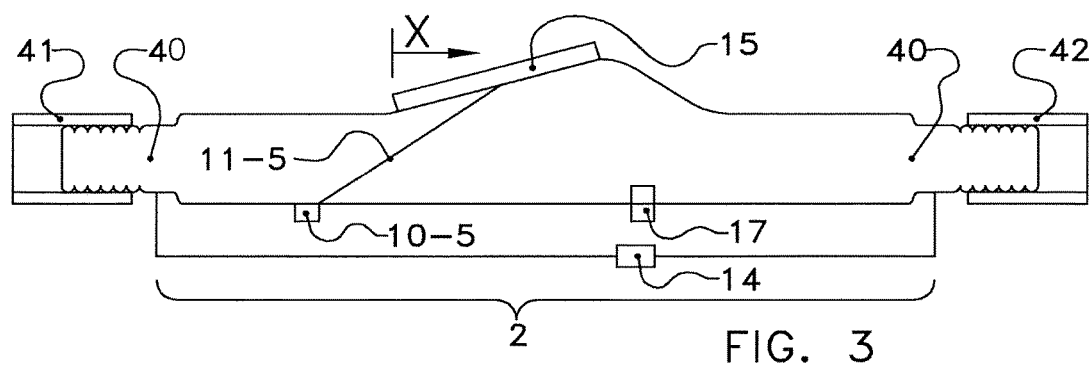
FIG. 3 shows a diagrammatic cross-sectional view of yet another sensor device according to the invention.

FIG. 3 shows a diagrammatic cross-sectional view of yet another sensor device according to the invention. In this case, a light source 10-5 is provided in the through-flow cell 2 which emits a beam 11-5 which is detected by a location-sensitive optical detector 15. Reference numeral 17 denotes a thermometer. Furthermore, reference numeral 40 denotes two hose nipples and reference numerals 41 and 42 denote a supply line and a discharge line, respectively.

The source 10-5 is shown with a beam 11-5 which passes through the liquid at an angle. Depending on the refractive index, and any boundary surface effects, the beam will strike the sensor 15 at a certain location and generate a signal there. If the liquid is homogenous and unchanging, said location will not change. If another liquid flows in which has a boundary surface or region with the first liquid, refraction and/or diffusion will occur at that boundary surface or region and the position on the sensor 15 will change. Such a change may be an indication of a liquid transition. In the figure, only an x-dependency is indicated. Of course, it is equally possible to detect a dependency at right angles thereto. The liquid transition dependency of the position will be significant if the beam 11-5 passes through the liquid (very) obliquely. Nevertheless, a (virtually) straight passage through the liquid is also an option but this is then extremely sensitive to effects, in particular diffusion, at the boundary surface, yet not at all to refractive index changes. A change in the surface of a light beam detected on the sensor 15 is also an indication of a refractive index or change thereof.

The through-flow cell is in this case made of a transparent material, such as a plastic, preferably a glass. This also serves as an insulator between two electrodes, in this case configured as hose nipples 40, of the conductivity or also impedance meter 14. Of course, the hose nipples which may, for example, be integrally moulded on, also serve to attach a supply line 41 and a discharge line 42 to the cell, if desired via means such as hose clamps.

The illustrated thermometer 17 serves to measure the temperature of the liquid and, like all other illustrated sensors, is connected to the sensor control. If the thermometer measures an absolute temperature which is too high or too low, which may, for example, result in physical danger for an animal, the sensor control can generate an alarm signal by means of a signal generator, such as an SMS message, an e-mail message or an audible and/or visible signal. According to the invention, it is an important possibility that the thermometer detects a temporary peak in the temperature. This virtually always indicates a reaction between two liquids at a boundary surface in between. On the basis thereof, it is also possible to determine a liquid transition indication in a highly reliable manner, if desired again with an alarm signal. It should be noted that a certain step in temperature in itself does not have to be an indication that an incorrect liquid is being supplied. After all, a new supply from a vessel stored in a cool manner may, for example, be provided. However, if there is a peak where the temperature is higher than both the first and the second liquid temperature, there has to be a cause therefor, which is often, if not always, due to a reaction between the liquids.

The light beam 11-5 is injected into the through-flow cell relatively obliquely since a refractive index change in the liquid which is present or even if the liquid is absent, may already cause a change in direction upon injection and thus a large change in position and/or beam surface change on the optical sensor 15.

Figure 4:
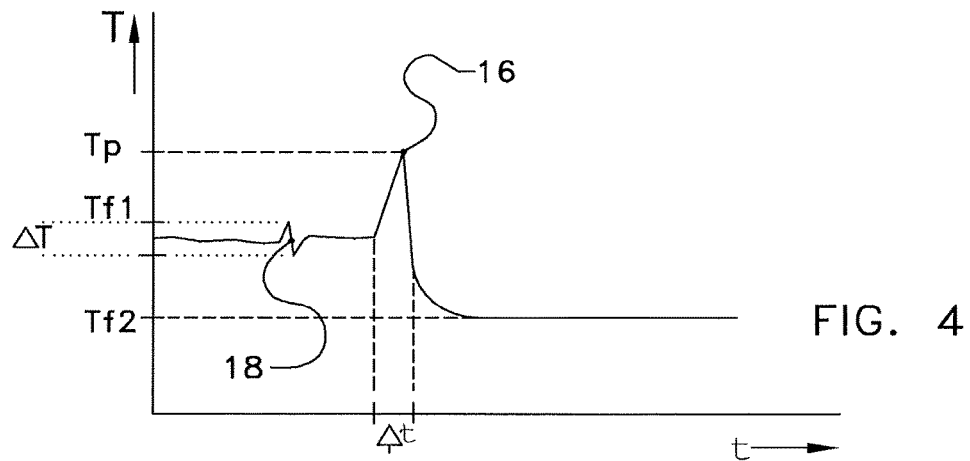
FIG. 4 shows a diagram with a possible measurement signal as a function of time.

FIG. 4 shows a diagram with a possible measurement signal T as a function of time t. The measurement signal relates to, for example, turbidity which can be determined from a transmission measurement or a temperature measurement. The measurement signal shows a peak 16 during a time $\Delta t$, and a noise ripple 18 of magnitude $\Delta T$. The value of the signal drops from a stable value Tf1 to a stable value Tf2. However, a peak 16 to a value Tp is situated in between.

In practice, the value of T will not be perfectly stable, but always contain a few noise ripples 18. However, in most cases, statistical research will be able to make a clear distinction between noise ripples 18 and a "real", causal peak 16, namely on the basis of the magnitude of the change in signal. In this case the increase (Tp−Tf1) and, because it is even greater, certainly the decrease (Tp−Tf2) are greater than an increase threshold value and a decrease threshold value, respectively, which in this case is 2$\Delta T$. This does not apply to the noise ripple 18. Therefore, while no alarm has to be emitted for the noise ripple, but an alarm does have to be generated for the peak 16. It should be noted that it is not necessary for both the increase and the decrease to exceed a threshold. If, for example, there is a considerable temperature difference between two liquids, the temperature increase might be hidden by the temperature step in combination with pure heat transportation and mixing resulting from a reaction. However, if there is nevertheless still an increase between the two stable levels, a reaction will also almost certainly have taken place here, and thus, not only the temperature has changed, but also the composition of the liquid, which may be a reason to emit an alarm.

Another important criterion is the time period during which a peak occurs. If this is a very wide, i.e. long, peak, this may equally well be an accidental general variation in temperature, for example as a result of solar radiation. Therefore, the time period $\Delta t$ is preferably also considered. If this is smaller than a specific value, which is to be determined in practice, a liquid transition is inferred and if not, no liquid transition is inferred. The time period may depend on the measured liquid flow velocity, but also, for example, on the distance to the liquid supply, such as the store or main line or the like. After all, in case of a large distance there may already be a greater degree of mixing and a peak will already be broader.

Figure 5:
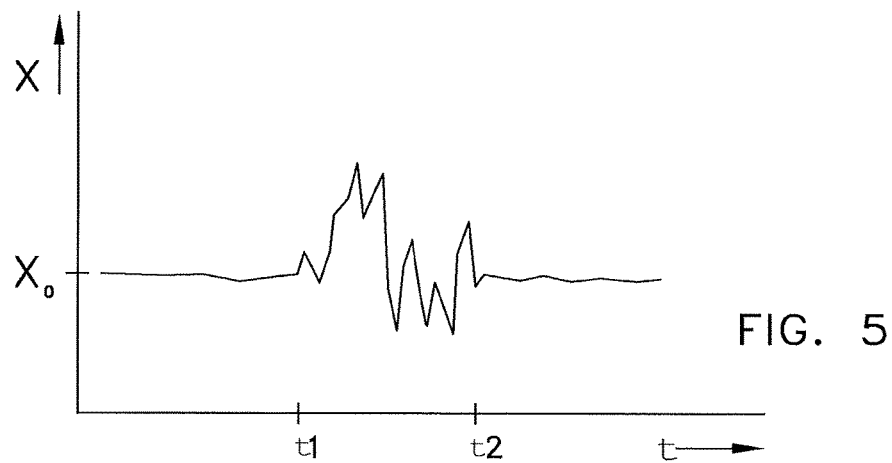
FIG. 5 shows a diagram with another possible measurement signal as a function of time.

FIG. 5 shows a diagram with another possible measurement signal as a function of time. This relates to an example of the x position of the beam 11-5 according to FIG. 3. As can be seen, this position is initially stable around X0, then varies greatly and then becomes stable around X0 again. This is an indication of a turbulent boundary surface which greatly disturbs the position of the light beam on the sensor 15, while the liquids themselves substantially have the same refractive index. It should be noted that there will then be a boundary region with a reaction product which will have a different refractive index. Alternatively, the beam travels through the liquid at right angles, and there is a refraction/reflection on a turbulent boundary surface, in particular if no mixing occurs.

Figure 6:
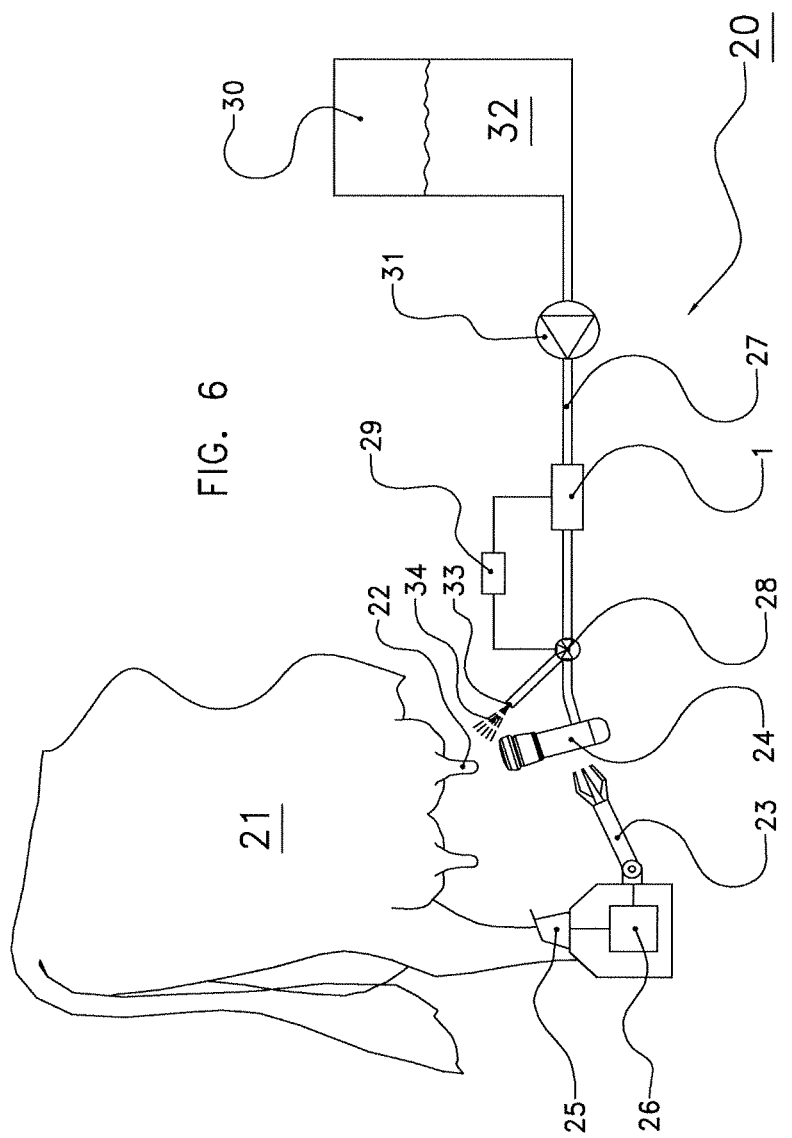
FIG. 6 shows a diagrammatic view of a teat treatment device according to the invention.

FIG. 6 shows a diagrammatic view of a dairy animal treatment device 20 according to the invention. Here, reference numeral 21 denotes a dairy animal with teats 22. In addition, there are present: a robot provided with a robot arm 23 and a teat detection system 25 and a robot control 26, as well as a teat cup 24, a liquid line 27, a valve 28, an alarm signal generator 29, a storage container 30 containing teat treatment liquid 32, and a pump 31, a spray nozzle 33 for a spray mist 34, as well as a sensor device 1 according to the invention.

The robot, controlled by the robot control 26, serves to connect the teat cup 24, for example, of a teat treatment device, in a manner known per se to a known robot arm 23 and teat detection device 25, which may incidentally be connected to the sensor control.

If the sensor device 1 determines that the liquid 32 in the through-flow cell and therefore in the storage container 30 is cause to emit an alarm, it will cause the alarm generator 29 to emit a signal and close valve 28 in line 27. Here, valve 28 is a three-way valve, wherein the sensor control can choose to allow liquid to pass to the teat cup 24, the spray nozzle 33 for applying a teat treatment agent by means of a spray mist 34, or not allowing liquid to pass. Thus, the danger to the dairy animal 21 is reduced. In addition, the sensor device 1 can actuate the robot control 26 directly or via the alarm signal via the robot control 26 in order to disconnect the teat cup 24.

Further modifications in addition to those described above may be made to the structures and techniques described herein without departing from the spirit and scope of the invention. Accordingly, although specific embodiments have been described, these are examples only and are not limiting upon the scope of the invention.

What is claimed is:

1. A dairy animal treatment device, comprising:
   a teat detection device for detecting the teats of a dairy animal;
   a teat treatment device for carrying out a teat-related operation on the teat;
   a robot arm with a control device configured to operatively bring the teat treatment device to at least one of the teats by means of the teat detection device;
   at least one liquid line; and
   a sensor system, the sensor system further comprising
      a through-flow cell in communication with the liquid line,
      a detector device for measuring a property of liquid in the through-flow cell and generating an associated detector signal, and
   a sensor control to analyze the detector signal, wherein the sensor control detects a liquid transition between two different liquids in the through-flow cell upon detecting at least one of (1) a change in the detector signal per unit time, (2) a change in the detector signal greater than a predetermined change threshold value, and (3) a change in the detector signal greater than a predetermined threshold value, wherein the change in the detector signal comprises at least one peak or trough in the detector signal, and wherein the peak or the trough has at least a predetermined magnitude.

2. The dairy animal treatment device according to claim 1, wherein the liquid line comprises a teat treatment liquid supply line and wherein the dairy animal treatment device is configured to apply teat treatment liquid for the teat treatment.

3. The dairy animal treatment device according to claim 1, further comprising a storage container for teat treatment liquid which is connected to the liquid line so as to be closable by a controllable valve,
wherein the control device is configured to make the controllable valve close the connection between the storage container and the liquid line on the basis of a generated alarm signal.

4. The dairy animal treatment device according to claim 1, further comprising a liquid presence detection mechanism configured to emit a liquid presence signal if liquid is present in the through-flow cell.

5. The dairy animal treatment device according to claim 1, wherein the sensor control is configured to generate an alarm signal if the sensor control detects a liquid transition.

6. The dairy animal treatment device according to claim 1, wherein the detector device comprises a temperature sensor which is configured to measure a temperature of the liquid in the through-flow cell.

7. The dairy animal treatment device according to claim 6, wherein the property comprises the temperature of the liquid and the sensor control is configured to generate an alarm signal if the temperature changes by more than a change threshold.

8. The dairy animal treatment device according to claim 7, wherein the sensor control generates an alarm signal if, within a predetermined time period, the temperature shows a peak of at least a predetermined magnitude, followed by a decrease by at least a predetermined decrease threshold.

9. The dairy animal treatment device according to claim 8, wherein the sensor control is configured to generate an alarm signal if, within a time period depending on the liquid flow velocity, the temperature shows an increase by at least a predetermined increase threshold, followed by a decrease by at least a predetermined decrease threshold.

10. The dairy animal treatment device according to claim 1, wherein the property comprises an optical property of the liquid.

11. The dairy animal treatment device according to claim 10, wherein the sensor control is configured to detect a liquid transition if the detector signal changes by more than a predetermined threshold change within a predetermined time period.

12. The dairy animal treatment device according to claim 10, the sensor system further comprising a light source to pass optical radiation through the through-flow cell, wherein the detector device comprises an optical detector to pick up and detect emitted optical radiation from the light source which has passed through the liquid.

13. The dairy animal treatment device according to claim 12, wherein at least one of (1) the light source, (2) a partial light source, and (3) an optical detector is provided around the through-flow cell, wherein the through-flow cell is translucent or transparent, at least at the location of said light source or partial light source.

14. The dairy animal treatment device according to claim 12, wherein the light source is configured to emit a light beam through the through-flow cell, and wherein the detector device comprises an optical sensor which is configured to detect a detection position on the optical sensor of the light beam which has passed through the through-flow cell.

15. The dairy animal treatment device according to claim 12, wherein the property comprises a detection position and the optical detector comprises an image recorder which is configured to record an image of the liquid in the through-flow cell, and wherein the sensor control comprises image-processing software to process the image and is configured to detect a liquid transition if the image shows a predetermined minimum change in time.

16. The dairy animal treatment device according to claim 15, wherein the image recorder comprises a video camera.

17. A dairy animal treatment device, comprising:
a teat detection device for detecting the teats of a dairy animal;
a teat treatment device for carrying out a teat-related operation on the teat;
a robot arm with a control device configured to operatively bring the teat treatment device to at least one of the teats by means of the teat detection device;
at least one liquid line; and
and a sensor system, the sensor system further comprising
a through-flow cell in communication with the liquid line,
a temperature sensor to measure a temperature of liquid in the through-flow cell and to generate an associated detector signal, and
a sensor control to analyze the detector signal,
wherein the sensor control is configured to detect a liquid transition between two different liquids in the through-flow cell upon detecting at least one of (1) a change in the detector signal per unit time, (2) a change in the detector signal greater than a predetermined change threshold value, and (3) a change in the detector signal greater than a predetermined threshold value, and
wherein the sensor control is configured to generate an alarm signal if the sensor control detects the liquid transition and if, within a predetermined time period, the temperature shows a peak of at least a predetermined magnitude, followed by a decrease by at least a predetermined decrease threshold.

18. The dairy animal treatment device according to claim 17, wherein the liquid line comprises a teat treatment liquid supply line and wherein the dairy animal treatment device is configured to apply teat treatment liquid for the teat treatment.

19. The dairy animal treatment device according to claim 17, further comprising a storage container for teat treatment liquid which is connected to the liquid line so as to be closable by a controllable valve,
wherein the control device is configured to make the controllable valve close the connection between the storage container and the liquid line on the basis of the generated alarm signal.

* * * * *